(12) United States Patent
Smouse

(10) Patent No.: US 8,657,884 B2
(45) Date of Patent: Feb. 25, 2014

(54) CONVERTIBLE NEPHROURETERAL CATHETER

(76) Inventor: Harry R. Smouse, Peoria, IL (US)

( * ) Notice: Subject to any disclaimer, the term of this patent is extended or adjusted under 35 U.S.C. 154(b) by 592 days.

(21) Appl. No.: 12/559,946

(22) Filed: Sep. 15, 2009

(65) Prior Publication Data

US 2010/0070047 A1 Mar. 18, 2010

Related U.S. Application Data

(60) Provisional application No. 61/096,902, filed on Sep. 15, 2008.

(51) Int. Cl.
*A61F 2/82* (2013.01)
*A61M 25/00* (2006.01)

(52) U.S. Cl.
USPC .............. 623/23.7; 623/23.64; 623/23.65; 623/23.66; 623/23.67; 604/8

(58) Field of Classification Search
USPC ............ 623/1.11, 1.15, 1.2, 1.22, 1.34, 623/23.64–23.67, 23.7; 604/8, 93.01, 604/96.01, 264, 523, 544, 349, 921
See application file for complete search history.

(56) References Cited

U.S. PATENT DOCUMENTS

| 4,350,161 | A | * | 9/1982 | Davis, Jr. ...................... 604/544 |
| 4,790,810 | A | * | 12/1988 | Pugh et al. ........................ 604/8 |
| 5,507,732 | A | * | 4/1996 | McClure et al. .............. 604/533 |
| 2007/0112420 | A1 | * | 5/2007 | LaDuca ...................... 623/1.44 |
| 2008/0140101 | A1 | * | 6/2008 | Carley et al. .................. 606/159 |

* cited by examiner

*Primary Examiner* — David Isabella
*Assistant Examiner* — Yashita Sharma
(74) *Attorney, Agent, or Firm* — McDonnell Boehnen Hulbert & Berghoff LLP

(57) ABSTRACT

A nephroureteral catheter is provided that comprises a detachable portion such that when the detachable portion is removed, the catheter converts into an internal stent. Catheter 100 allows drainage of urine into the bladder and externally into a bag. The catheter includes a tube having a circular cross section, a detachable portion, a locking mechanism, an inner tube, a first pigtail curl, a second pigtail curl, and a marker. The marker indicates the tube end. The tube includes a first end, a second end, and a plurality of holes. The detachable portion is attached to the tube with the inner tube, as the inner tube is placed and is friction sealed to the walls of a hollow portion that extends through both the detachable portion and a section of the tube. The inner tube may be removed from within the tube, past the marker that indicates the end of the tube, so that detachable portion is now removable from within the patient's body. When the detachable portion is attached to the catheter, the catheter is a nephroureteral catheter. When the detachable portion is removed from the catheter, the catheter becomes a stent.

16 Claims, 3 Drawing Sheets

CONVERTIBLE NEPHROURETERAL CATHETER

FIELD

The present invention relates generally to catheters. More particularly, the present invention relates to a nephroureteral catheter.

BACKGROUND

Many patients experience the development of a stricture or blockage within the ureter of one or both kidneys. The ureter is the muscular tube that connects the kidney to the bladder. As urine is made by the kidney it drains into a central collecting system of the kidney and then travels though the ureter into the bladder. Patients can develop strictures, or blockages, of the ureter due to kidney stones, cancers, infections, trauma, and prior medical instrumentations. In rare instances, some children are born with blockages of one or both ureters. If untreated, the blockage will eventually lead to kidney failure.

Regardless the cause, the treatment for a blocked ureter is to relieve the blockage. Blockage removal is performed by inserting a long tube to connect the collecting system of the kidney to the bladder. This tube is called a stent and is placed through the ureter.

Stent insertion is typically performed by one of two methods. The stent may be inserted urologically. With this method, a scope is advanced through the urethra into the bladder. A wire is then inserted into the ureter in a retrograde fashion, using the scope to thread the wire. When the wire reaches the collecting system of the kidney, a plastic stent is inserted over the wire. The stent is a straight plastic tube that has a pigtail-shaped curl on each end. Once in place, the wire is removed and the scope is taken out of the bladder. One pigtail curl of the stent resides in the collecting system of the kidney and the other resides in the bladder. The straight portion of the stent traverses the ureter. This is performed using direct visualization with the scope and also with fluoroscopic guidance. The stent usually stays in for a period of approximately three months, at which point the stent is then swapped out for a new stent by the urologist using a similar technique.

The second method for insertion is to insert the stent percutaneously. This method is typically performed in stages. The right or left flank of the patient is sterilely prepared depending upon which kidney is to be accessed (sometimes both are accessed to treat bilateral blockages). Intravenous sedation is used. A small bore needle is used to puncture the collecting system of the kidney and contrast is injected allowing the complete visualization of the entire collecting system. The central portion is initially punctured with a small needle, and then a larger needle is used to puncture a smaller but safer area of the collecting system. A guidewire is threaded into the collecting system of the kidney and a pigtail drain, or nephrostomy catheter, is placed, sutured to the back, and hooked up to a bag for external drainage. Once the urine has cleared from bleeding, the patient is brought back to the angiography table, placed prone, and a wire is inserted through the catheter into the kidney. The catheter is then removed. The wire is threaded through the ureter into the bladder (across the stricture) and a nephroureteral catheter is placed.

A nephroureteral catheter is a long plastic tube that goes from the outside of the patient into the kidney's collecting system, through the ureter, and into the bladder. The catheter allows drainage of urine into the bladder and externally into a bag. The catheter typically stays in the patient for 7-10 days, at which time the patient is brought back to the angiography table and a wire is threaded through this tube into the bladder. The tube is removed and an internal stent is placed using fluoroscopic guidance. This is the same type of stent that is placed by the urologist working through the bladder. This can be a complex and difficult procedure.

SUMMARY

In accordance with the present invention, a nephroureteral catheter is provided that comprises a detachable portion such that when the detachable portion is removed, the catheter converts into an internal stent.

The catheter includes a tube having a circular cross section, a detachable portion, a locking mechanism, an inner tube, a first pigtail curl, a second pigtail curl, and a marker. The marker indicates the end of the tube. The catheter includes a first end, a second end, and a plurality of holes. The detachable portion is attached to the tube with the inner tube, as the inner tube is placed and is friction sealed to the walls of a hollow portion that extends through both the detachable portion and a section of the tube. The inner tube may be removed from within the tube, past the marker that indicates the end of the tube, so that detachable portion is now removable from within the patient's body, leaving an internal stent in the body.

The convertible nephroureteral catheter eliminates the step of removing a nephroureteral catheter and placing a new internal stent into a patient. Because a step is eliminated, the convertible nephroureteral catheter saves time. Instead of a physician having to take steps such as sterile prep to place a new catheter inside a patient, the physician need only unlock the hub of the convertible nephroureteral catheter to detach the external portion of the catheter. Money is also saved since one less catheter will be required. In addition, other supplies such as wires, sheaths, and other equipment needed to place a typical internal catheter will be spared. The patient will only be subjected to minimal, if any, radiation from fluoroscopy.

The convertible nephroureteral catheter will also result in less patient discomfort, again due to minimal manipulation because less steps are required. With previous stent insertion procedures, local and IV sedation and nursing monitoring were required. Patients will not require sedation for the process of removing the removable portion of the convertible nephroureteral catheter. The new procedure for transforming the convertible nephroureteral catheter may be performed at bedside.

The convertible nephroureteral catheter allows for the catheter insertion process to be a single step instead of a multiple-step process. The ability to insert a catheter percutaneously with a single step might provide an advantage over urological insertion, as they will both now require only a single step for insertion, yet using the convertible nephroureteral catheter will not require the general anesthesia required by urological insertion.

BRIEF DESCRIPTION OF THE DRAWINGS

Various embodiments are described herein with reference to the following drawings. Certain aspects of the drawings are depicted in a simplified way for reason of clarity. Not all alternatives and options are shown in the drawings and, therefore, the invention is not limited in scope to the content of the drawings. In the drawings.

DETAILED DESCRIPTION

Figure 1:
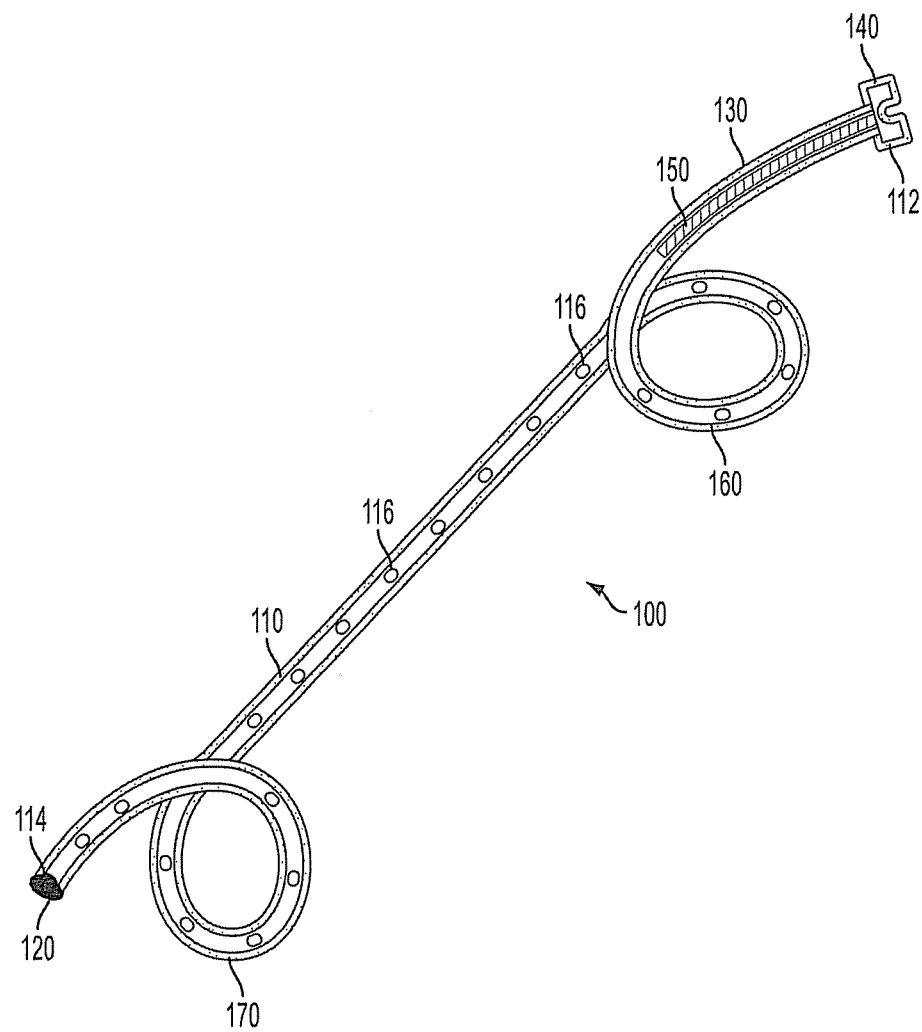
FIG. 1 is a perspective view of the nephroureteral catheter.

FIG. 1 depicts a perspective view of a catheter 100 according to one embodiment of the present invention. Catheter 100 is provided for use as a nephroureteral catheter.

Figure 3:
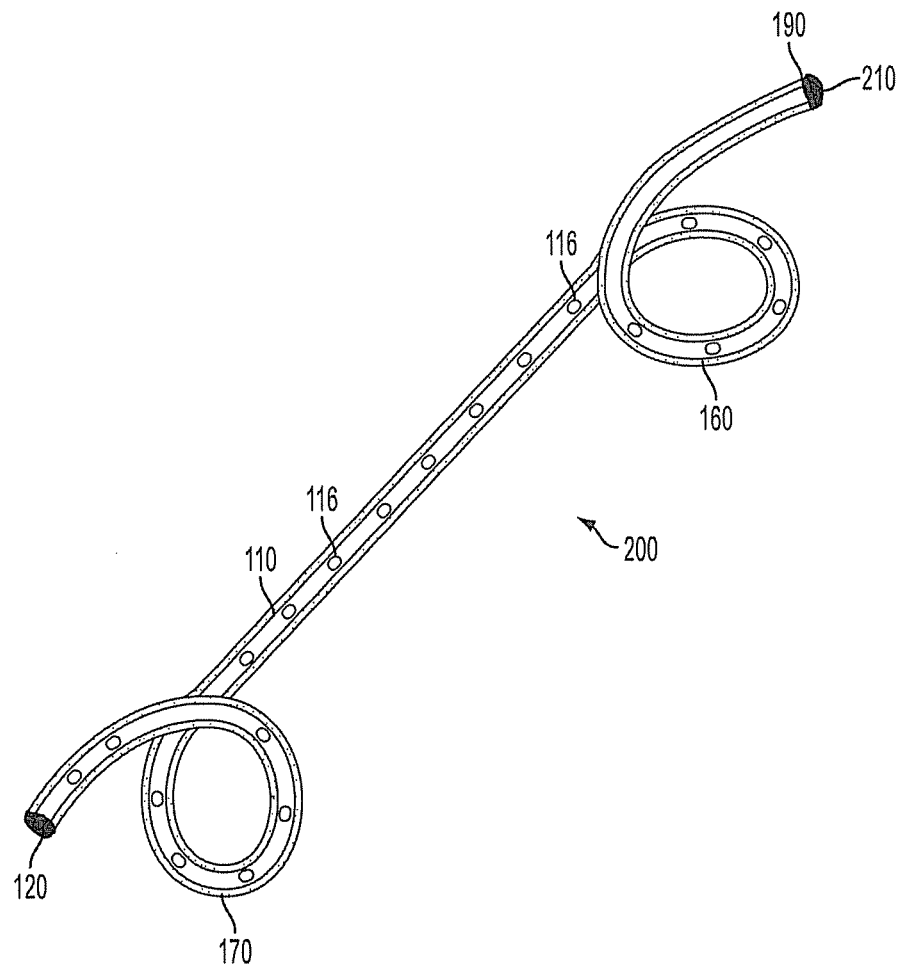
FIG. 3 is a perspective view of the stent that remains after the detachable portion has been removed.

Catheter 100 allows for the drainage of urine into the bladder and externally into a bag. Catheter 100 includes a tube 110 having a circular cross section 120, a detachable portion 130, a locking mechanism 140, an inner tube 150, a first pigtail curl 160, a second pigtail curl 170, and a marker 190. Catheter 100 also includes a first end 112, a second end 114, and a plurality of holes 116. When detachable portion 130 is attached to the catheter, catheter 100 is a nephroureteral catheter. When detachable portion 130 is removed from the catheter, the catheter becomes a stent 200, as shown in FIG. 3.

Tube 110 may be flexible. The tube 110 has a hollow interior to allow for fluids to flow through the tube. Plurality of holes 116 extend through tube 110 so that fluids may flow into or out of tube 110 through the holes. Tube 110 is of sufficient length so that it extends from the outside of the patient into the kidney, through the ureter and into the bladder.

First pigtail curl 160 and second pigtail curl 170 serve the purpose of keeping or retaining tube 110 in the proper position within the patient. First pigtail curl 160 is located near first end 112 and second pigtail curl 170 is near second end 114, so that first pigtail curl 160 lies within the collecting system of the kidney and second pigtail curl 170 lies within the bladder. Each curl ensures tube 110 will not move out of the ureter, because each curl is too large to pass through the ureter. Second pigtail curl 170 enters the ureter in a straight position, but the material of tube 110 at the section of second pigtail curl 170 is such that it will bend into the curl position shown in FIG. 1 after the tube has room to bend, or once it has exited the ureter.

Figure 2:
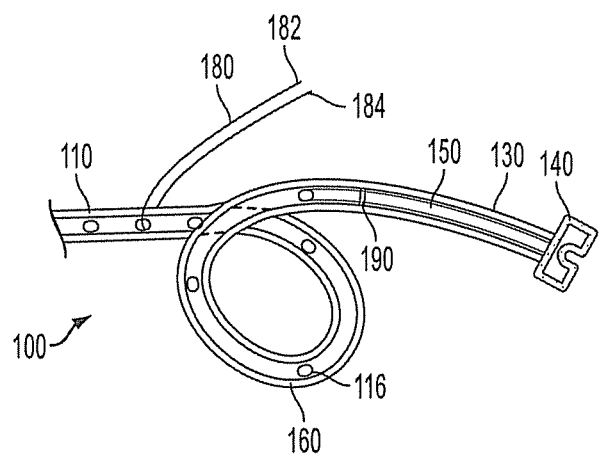
FIG. 2 is a perspective view of the detachable portion of the nephroureteral catheter of FIG. 1.

First pigtail curl enters the kidney in the straight position as well, and may also bend into the curl position once in place. However, to help first pigtail curl bend to the proper position, a string 180 may be pulled through a hole of the plurality of holes 116, as shown in FIG. 2, and the string may be manually pulled on both ends 182, 184 until first pigtail curl is set in place. Thereafter, string 180 may be manually removed by pulling one of ends 182, 184. String 180 may be a suture. Alternatively, string 180 may be a number of other materials.

Locking mechanism 140 may be a number of locking mechanisms currently used in the art. Locking mechanism closes off detachable portion 130 of tube 110, and may be manually opened and removed to access any of detachable portion 130, inner tube 150, or tube 110.

Detachable portion 130 may be made from the same material as tube 110. Detachable portion 130 may be flush with tube 110 at marker 190. Detachable portion 130 comprises a hollow section within which inner tube 150 may slide through. Inner tube may extend through a portion of tube 110, as shown in FIG. 2. Inner tube 150 comprises a hollow interior to allow for fluid to flow through the interior of inner tube 150. Fluid is exchanged between tube 110 and inner tube 150 through the hollow interior of inner tube 150. Tube 110 also comprises at least a portion of a hollow section within which inner tube 150 may slide through. The hollow portion of tube 110 comprises a smaller radius than the remainder of the hollow interior of tube 110. The hollow portions of both the detachable portion 130 and tube 110 are sized such that when inner tube is inside the hollow portions, there is a friction seal between the exterior surface of inner tube 150 and the walls of the hollow portions. However, inner tube 150 may be attached to tube 110 and detachable portion 130 in a number of other ways. For example, in an alternative embodiment, inner tube 150 may comprise threads on its exterior surface that correspond to threads along the walls of the hollow interior of tube 110, and thus to remove inner tube 150 from tube 110, inner tube 150 must be unscrewed from tube 110. In another alternative embodiment, detachable portion 130 may comprise a smaller circumference than tube 110 such that detachable portion 130 may also fit within the hollow portion of tube 110, for example, 2 or 3 mm into tube 110. Thus when inner tube 150 is in place within both tube 110 and detachable portion 130, inner tube 150 pushes outward on detachable portion 130, which in turn presses on tube 110, resulting in a tighter fit. In this embodiment, detachable portion 130 may still be manually removed from tube 110 after the removal of inner tube 150 from tube 110.

Detachable portion 130 may be manufactured as part of catheter 100. When attached to catheter 100 and in place inside a patient, detachable portion 130 extends from the center of the kidney to an exit in the back of the patient, ending with locking mechanism 140, which is located outside the patient's body.

FIG. 3 shows a perspective view of a stent 200 that remains after the detachable portion has been removed. Stent 200 comprises the same tube 110 as catheter 100, with first pigtail curl 160 and second pigtail curl 170 untouched within the body of the patient. Detachable portion 130, inner tube 150, and locking mechanism 140 have been removed. A new end 210 is at marker 190.

In operation, the right or left flank of the patient is sterilely prepared depending upon which kidney is to be accessed. Intravenous sedation is used. A small bore needle is used to puncture the collecting system of the kidney and contrast is injected allowing the complete visualization of the entire collecting system. The central portion is initially punctured with a small needle, and then a larger needle is used to puncture a smaller but safer area of the collecting system. A guidewire is threaded into the collecting system of the kidney and a pigtail drain, or nephrostomy catheter, is placed, sutured to the back, and hooked up to a bag for external drainage.

Once the urine has cleared from bleeding, the patient is brought back and a wire is inserted through the catheter into the kidney and the catheter is removed. The wire is threaded through the ureter into the bladder (across the stricture) and catheter 100 is placed. Pigtail curls 160, 170 are curled to their proper position. The catheter typically stays in the patient for 7-10 days, at which time the patient is brought back.

At this point, if the physician desires to exchange the catheter 100 for a stent 200, the physician will unlock locking mechanism 140, and will remove the locking mechanism to access inner tube 150. The physician will then manually pull inner tube 150 through the hollow portion of tube 110 toward first end 112, until inner tube 150 has been pulled past marker 190 and is no longer within the hollow portion of tube 110. Once inner tube 150 has been removed from tube 110, detachable portion 130 is no longer attached to tube 110 and both detachable portion 130 and inner tube 150 may be removed from the patient's body. Once detachable portion 130 and inner tube 150 are removed, catheter 100 becomes a stent 200, as shown in FIG. 3. This is same type of stent that would typically be placed by the urologist working through the bladder. Stent 200 now comprises a new end 210 that is located at marker 190.

An example of when the convertible nephroureteral catheter may be used is a situation in which a patient has a blockage of the ureter and presents with hydronephrosis (dilation of the kidney's collecting system) and hydroureter (dilation of the ureter). The patient has a device inserted through the flank, into the collecting system, and through the ureter into the bladder. The device will be left open to external drainage until the urine clears from infection or bleeding. When the urine has cleared, the external portion of the convertible nephroureteral catheter 100 will be detached, converting the catheter into an internal stent. From this point forward, the stent will drain urine directly from the kidney to the bladder. The internal stent will remain in place until it is ready to be removed or replaced.

Another example of use is when a patient recently passed a kidney stone and the ureter is temporarily inflamed and blocked. The convertible nephroureteral catheter is inserted in the same manner described above. In this situation, however, the catheter is left in place temporarily until the inflammation improves; once this is confirmed, the entire catheter is removed by pulling it out of the flank with contrast injection under fluoroscopy. In this situation the detachable portion is not detached. However, the catheter may also be left in place as an internal stent, and the detachable portion removed, depending on the clinical need.

Another example of use is when a patient has leakage from the ureter due to trauma, instrumentation, stone removal, cancer, or another reason, and internal and external urine diversion is necessary. In this case, convertible nephroureteral catheter 100 is placed in the patient and urine is allowed to drain externally. When there is improvement in the leakage and the catheter is converted to an internal stent by removing detachable portion 130, internal urine diversion is allowed for a longer period of time. The stent 200 will be removed at a later date after the leak is resolved.

It will thus be seen that certain changes may be made in the above constructions without departing from the spirit and scope of the invention. It is intended that all matter contained in the above description or shown in the accompanying drawings shall be interpreted as illustrative and not in a limiting sense.

I claim:

1. A catheter, comprising:
    a tube comprising a first end, a second end, a first retention feature near the first end, and a second retention feature near the second end;
    a detachable portion, wherein the detachable portion is in fluid communication with and is removably attachable to the tube at the second end, and is configured to be placed within a patient and thereby extend from the center of the kidney to the back of the patient; and
    an inner tube, wherein the inner tube is removably insertable into and attachable to both the tube and the detachable portion;
    wherein when the detachable portion is attached to the second end, the second end is positioned between the second retention feature and the detachable portion such that when the detachable portion is removed from the tube at the second end, the second retention feature remains on the tube,
    wherein once the inner tube and the detachable portion are removed from the tube, the catheter functions as an internal stent.

2. The catheter of claim 1, wherein the first retention feature and the second retention feature comprise a first curl and a second curl, respectively.

3. The catheter of claim 2, further comprising a plurality of holes extending through an exterior surface of the tube.

4. The catheter of claim 1, further comprising a locking mechanism at a first end of the detachable portion, wherein the locking mechanism is configured to open and close, and wherein when closed, the locking mechanism prevents access to an interior of the detachable portion.

5. The catheter of claim 1, wherein the tube comprises a circular cross-section.

6. The catheter of claim 1, further comprising a friction seal between an exterior surface of the inner tube and the detachable portion.

7. A nephroureteral catheter that converts into a stent, comprising:
    a tube, wherein the tube comprises a hollow portion, a first end, a second end, a first retention feature near the first end, and a second retention feature near the second end;
    a detachable portion, wherein the detachable portion comprises a hollow portion and is attached at the second end of the tube; and
    an inner tube extending through at least a section of both the hollow portion of the tube and the hollow portion of the detachable portion, wherein once the inner tube is removed, the detachable portion is removable from the tube; wherein when the detachable portion is attached to the second end, the second end is positioned between the second retention feature and the detachable portion such that when the detachable portion is removed from the tube at the second end, the second retention feature remains on the tube, wherein once the inner tube and the detachable portion are removed from the tube, the catheter functions as an internal stent.

8. The nephroureteral catheter of claim 7, wherein the detachable portion is the portion of the tube that extends from the center of the kidney to the back of the patient when the nephruoreteral catheter is in place in the patient.

9. The nephroureteral catheter of claim 7, further comprising a first curl and a second curl as the first retention feature and the second retention feature, respectively.

10. The nephroureteral catheter of claim 7, wherein the tube comprises a plurality of holes that extend through the tube.

11. A convertible catheter comprising:
    a tube comprising an exterior surface, a hollow interior, a first end, a second end, a first retaining feature near the first end and a second retaining feature near the second end, wherein a portion of the tube is detachable at a location between the second retaining feature and the second end; and
    an inner tube, wherein the inner tube is removably insertable into the tube and extends into the detachable portion of the tube,
    wherein the second retaining feature is not detachable from the tube and wherein once the inner tube and the detachable portion are removed from the tube, the catheter functions as an internal stent.

12. The convertible catheter of claim 11, wherein the hollow interior of the tube is configured for fluid passage therethrough.

13. The convertible catheter of claim 11, further comprising a plurality of holes extending through the exterior surface of the tube into the hollow interior.

14. The convertible catheter of claim 13, wherein the plurality of holes allows for fluid flow through the holes.

15. The convertible catheter of claim 11, wherein the catheter is configured to be inserted into a patient and extend from outside a patient to a patient's bladder.

16. The convertible catheter of claim 11, wherein when inserted into the tube, an exterior surface of the inner tube forms a friction seal with an interior surface of the tube.

* * * * *